United States Patent
Bambal et al.

(10) Patent No.: US 10,479,742 B2
(45) Date of Patent: *Nov. 19, 2019

(54) LIQUID PHASE XYLENE ISOMERIZATION IN THE ABSENCE OF HYDROGEN

(71) Applicant: UOP LLC, Des Plaines, IL (US)

(72) Inventors: Ashish Suresh Bambal, Arlington Heights, IL (US); Gregory B. Kuzmanich, Arlington Heights, IL (US); Patrick C. Whitchurch, Sleepy Hollow, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/487,354

(22) Filed: Apr. 13, 2017

(65) Prior Publication Data

US 2017/0297977 A1 Oct. 19, 2017

Related U.S. Application Data

(60) Provisional application No. 62/322,672, filed on Apr. 14, 2016.

(51) Int. Cl.
C07C 5/27 (2006.01)
C07C 5/22 (2006.01)

(52) U.S. Cl.
CPC ........ C07C 5/2775 (2013.01); C07C 2529/70 (2013.01)

(58) Field of Classification Search
CPC ..... C07C 5/2775; C07C 2529/70; C07C 5/22; C07C 5/277; C07C 5/2732; C07C 5/2735
See application file for complete search history.

(56) References Cited

U.S. PATENT DOCUMENTS

| | | | |
|---|---|---|---|
| 2,620,314 A | 12/1952 | Hoekstra | |
| 3,835,198 A | 9/1974 | Myers | |
| 4,152,297 A | 5/1979 | Kamiyama et al. | |
| 4,229,424 A | 10/1980 | Kokotailo et al. | |
| 4,283,583 A | 8/1981 | Velenyi et al. | |
| 4,783,568 A | 11/1988 | Schmidt | |

(Continued)

FOREIGN PATENT DOCUMENTS

| | | |
|---|---|---|
| CN | 102822127 A | 12/2012 |
| JP | 55144413 S | 11/1980 |

(Continued)

OTHER PUBLICATIONS

Grandio, "Xylene Isomerization Over Zeolite Catalysts", General Papers Sessions on Petrochemicals presented before the Division of Petroleum Chemistry, Inc.; American Chemical Society; Washington Meeting, Sep. 12-17, 1971, B70-B76.

(Continued)

*Primary Examiner* — Youngsul Jeong

(57) ABSTRACT

The field of this claimed subject matter generally relates to liquid phase isomerization technology. More specification, the field relates to liquid phase isomerization in complete absence of hydrogen which eliminates the need for gas-liquid separation at the reactor outlet. Even in the absence of the hydrogen, the catalyst demonstrates a stable isomerization performance with a paraxylene to xylene ratio of about 23 wt % in the product stream.

8 Claims, 1 Drawing Sheet

$$\text{Relative activity} = \frac{\left(\frac{pX}{X}\right)_t}{\left(\frac{pX}{X}\right)_{t=0}}$$

- A: UZM-54 with Silica binder, H2/HCBN = 0.05 mol
- B: UZM-54 with Silica binder, H2/HCBN = 0 mol
- C: UZM-54 with Alumina binder, H2/HCBN = 0.05 mol
- D: UZM-54 with Alumina binder, H2/HCBN = 0 mol

(56) References Cited

U.S. PATENT DOCUMENTS

| | | |
|---|---|---|
| 6,376,730 B1 | 4/2002 | Jan et al. |
| 6,504,075 B2 | 1/2003 | Beck et al. |
| 6,740,788 B1 | 5/2004 | Maher et al. |
| 7,314,601 B2 | 1/2008 | Negiz et al. |
| 7,368,620 B2 | 5/2008 | Zhou et al. |
| 7,371,913 B2 | 5/2008 | Bauer |
| 7,495,137 B2 | 2/2009 | Zhou et al. |
| 7,982,084 B1 | 7/2011 | Moscoso et al. |
| 8,058,496 B2 | 11/2011 | Bogdan et al. |
| 8,071,831 B1 | 12/2011 | Bogdan et al. |
| 8,697,929 B2 | 4/2014 | Ou et al. |
| 8,716,541 B2 | 5/2014 | Ou |
| 9,227,888 B2 | 1/2016 | Porter |
| 9,266,794 B1 | 2/2016 | Ou et al. |
| 9,890,094 B2 | 2/2018 | Kuzmanich et al. |
| 2005/0131261 A1* | 6/2005 | Nemeth ............... C07C 5/2708 585/481 |
| 2007/0004947 A1 | 1/2007 | Zhou et al. |
| 2007/0004948 A1 | 1/2007 | Bauer |
| 2008/0299289 A1 | 12/2008 | Fisk |
| 2009/0182182 A1 | 7/2009 | Bauer |
| 2011/0245565 A1 | 10/2011 | Bogdan et al. |
| 2015/0175507 A1 | 6/2015 | Bender et al. |
| 2016/0257631 A1* | 9/2016 | Kuzmanich ............ C07C 5/2737 |
| 2016/0257632 A1* | 9/2016 | Kuzmanich ............. C01B 39/36 |

FOREIGN PATENT DOCUMENTS

| | | |
|---|---|---|
| JP | 2008001699 A | 1/2008 |
| JP | 2009500323 A | 1/2009 |
| JP | 2009500324 A | 1/2009 |
| JP | 2013528576 A | 7/2013 |
| TW | 200710078 A | 3/2007 |
| TW | 200738612 A | 10/2007 |
| TW | 201202141 A | 1/2012 |

OTHER PUBLICATIONS

Search Report dated Aug. 14, 2017 for corresponding PCT Appl. No. PCT/US2017/026786.

* cited by examiner

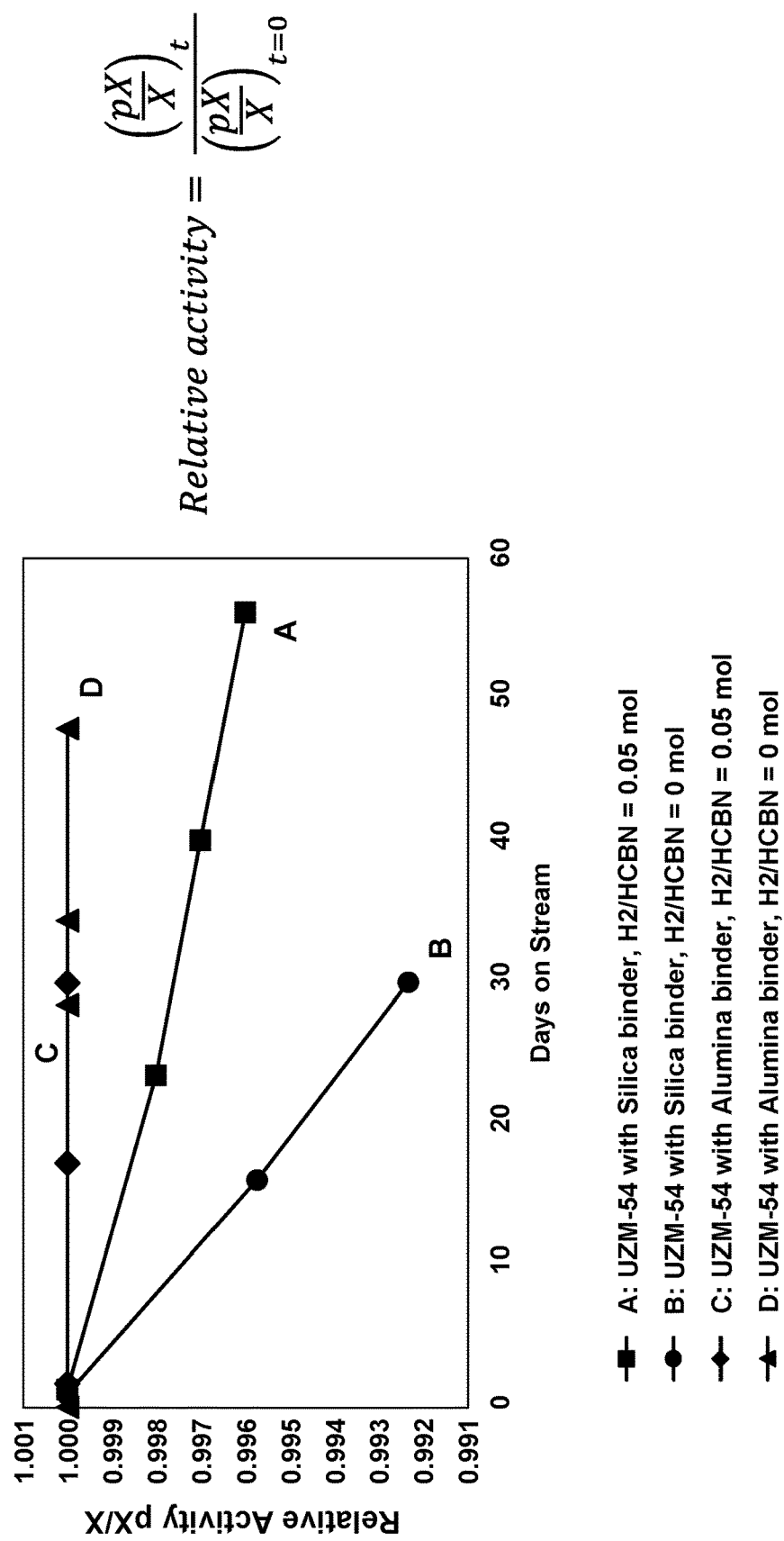

LIQUID PHASE XYLENE ISOMERIZATION IN THE ABSENCE OF HYDROGEN

CROSS-REFERENCE TO RELATED APPLICATION

This application claims priority from Provisional Application No. 62/322,672 filed Apr. 14, 2016, the contents of which cited application are hereby incorporated by reference in its entirety.

FIELD

The field of the claimed subject matter generally relates to liquid phase isomerization technology. More specification, the field relates to liquid phase isomerization wherein the isomerization catalyst comprises UZM-54, a binder, and no metals in the complete absence of hydrogen which eliminates the need for gas-liquid separation at the reactor outlet.

BACKGROUND

The xylenes, such as para-xylene, meta-xylene and ortho-xylene, can be important intermediates that find wide and varied application in chemical syntheses. Generally, para-xylene upon oxidation yields terephthalic acid that is used in the manufacture of synthetic textile fibers and resins. Meta-xylene can be used in the manufacture of plasticizers, azo dyes, and wood preservers. Generally, ortho-xylene is a feedstock for phthalic anhydride production.

Xylene isomers from catalytic reforming or other sources generally do not match demand proportions as chemical intermediates, and further comprise ethylbenzene, which can be difficult to separate or to convert. Typically, para-xylene is a major chemical intermediate with significant demand, but amounts to only about 20% to about 25% of a typical $C_8$ aromatic stream. Adjustment of an isomer ratio to demand can be effected by combining xylene-isomer recovery, such as adsorption for para-xylene recovery, with isomerization to yield an additional quantity of the desired isomer. Typically, isomerization converts a non-equilibrium mixture of the xylene isomers that is lean in the desired xylene isomer to a mixture approaching equilibrium concentrations. It is also desirable to convert ethylbenzene to benzene while minimizing xylene loss. Moreover, other desired aromatic products, such as benzene, can be produced from such processes.

BRIEF SUMMARY

A first embodiment of the claimed subject matter is a process for the isomerization of an alkylaromatic feed mixture, comprising contacting the alkylaromatic feed mixture in a $C_8$ isomerization zone, wherein the $C_8$ isomerization zone comprises an isomerization stage wherein the alkylaromatic feed mixture contacts a catalyst comprising a UZM-54, a binder, and an absence of metals, at isomerization conditions in a liquid phase in the substantial absence of hydrogen to produce a product stream. An embodiment of the claimed subject matter is one, any or all of prior embodiments in this paragraph up through the first embodiment in this paragraph, wherein the binder may be alumina. In another embodiment, the catalyst may comprise a layered MFI, a two dimensional layered MFI structure.

Even in the absence of the hydrogen, the catalyst demonstrates a stable isomerization performance with a paraxylene to xylene ratio of about 23 wt % in the product stream. Further, a stable catalyst even in hydrogen absence would enable uninterrupted liquid phase isomerization operation without any need for regeneration.

Definitions

As used herein, the term "zone" can refer to an area including one or more equipment items and/or one or more sub-zones. Equipment items can include one or more reactors or reactor vessels, heaters, separators, exchangers, pipes, pumps, compressors, and controllers. Additionally, an equipment item, such as a reactor or vessel, can further include one or more zones or sub-zones.

As used herein, the term "stream" can be a stream including various hydrocarbon molecules, such as straight-chain, branched, or cyclic alkanes, alkenes, alkadienes, and alkynes, and optionally other substances, such as gases, e.g., hydrogen, or impurities, such as heavy metals. The stream can also include aromatic and non-aromatic hydrocarbons. Moreover, the hydrocarbon molecules may be abbreviated $C_1, C_2, C_3 \ldots C_n$ where "n" represents the number of carbon atoms in the hydrocarbon molecule.

As used herein, the term "aromatic" can mean a group containing one or more rings of unsaturated cyclic carbon radicals where one or more of the carbon radicals can be replaced by one or more non-carbon radicals. An exemplary aromatic compound is benzene having a $C_6$ ring containing three double bonds. Other exemplary aromatic compounds can include para-xylene, ortho-xylene, meta-xylene and ethylbenzene. Moreover, characterizing a stream or zone as "aromatic" can imply one or more different aromatic compounds.

As used herein, the term "support" generally means a molecular sieve that has been combined with a binder before the addition of one or more additional catalytically active components, such as a metal, or the application of a subsequent process such as reducing, sulfiding, calcining, or drying. However, in some instances, a support may have catalytic properties and can be used as a "catalyst".

As used herein, the term "non-equilibrium" generally means at least one $C_8$ aromatic isomer can be present in a concentration that differs substantially from the equilibrium concentration at a different isomerization condition.

As used herein, the term "substantial absence of hydrogen" means that no free hydrogen is added to a feed mixture and that any dissolved hydrogen from prior processing is substantially less than about 0.05 moles/mole of feed, frequently less than about 0.01 moles/mole, and possibly not detectable by usual analytical methods.

As used herein, the term "layered MFI" means a two dimensional layered MFI structure.

BRIEF DESCRIPTION OF THE DRAWING

The FIGURE is a graph illustrating a stability comparison for the liquid phase isomerization catalyst.

DETAILED DESCRIPTION

An exemplary aromatic production facility can include a xylene isomer separation zone, a $C_8$ isomerization zone, and a separation zone. The aromatic production facility can include other zones or units, such as an alkylation, an extractive distillation, and/or an olefin saturation zone or unit, as disclosed in, for example, U.S. Pat. No. 6,740,788 B1.

The xylene isomer, such as a para-xylene or meta-xylene, separation zone can receive an alkylaromatic feed mixture in a line. Typically, the feed mixture may be derived from any of a variety of original sources, e.g., petroleum refining, thermal or catalytic cracking of hydrocarbons, coking of coal, or petrochemical conversions in, e.g., a refinery or petrochemical production facility. Preferably the feed mixture is found in appropriate fractions from various petroleum-refinery streams, e.g., as individual components or as certain boiling-range fractions obtained by the selective fractionation and distillation of catalytically cracked or reformed hydrocarbons.

The xylene isomer separation zone can include one or more reactors to produce an extract of a desired isomer, such as para-xylene, in a line and a raffinate in a line. The xylene isomer separation zone may be based on a fractional crystallization process or an adsorptive separation process. An adsorptive separation process can recover over about 99%, by weight, para-xylene in the line at high recovery per pass. An exemplary xylene isomer separation zone is disclosed in U.S. Pat. No. 6,740,788 B1. The raffinate, which is an effluent from the zone, can be sent via the line and a line to the $C_8$ isomerization zone.

Typically, the raffinate substantially comprises the alkylaromatic feed mixture in the line. The alkylaromatic feed mixture can include isomerizable alkylaromatic hydrocarbons of the general formula $C_6H_{(6-n)}R_n$, where n is an integer of 1-5 and R is $CH_3$, $C_2H_5$, $C_3H_7$, or $C_4H_9$, in any combination suitable for isomerization to obtain at least one more valuable alkylaromatic isomer, such as para-xylene or meta-xylene, in an isomerized product. The feed mixture can include one or more ethylaromatic hydrocarbons containing at least one ethyl group, i.e., at least one R of at least one of the alkylaromatic hydrocarbons is $C_2H_5$. Suitable components of the feed mixture generally include, for example, an ethylbenzene, a meta-xylene, an ortho-xylene, a para-xylene, an ethyl-toluene, a trimethylbenzene, a diethyl-benzene, a triethylbenzene, a methylpropylbenzene, an ethylpropylbenzene, a diisopropylbenzene, or a mixture thereof. Typically, the one or more ethylaromatic hydrocarbons are present in the feed mixture in a concentration of about 2% to about 100%, by weight.

Usually the feed mixture is prepared by removal of para-, ortho- and/or meta-xylene from a fresh $C_8$ aromatic mixture obtained from one or more aromatic-production or aromatic-conversion processes to yield a stream depleted in at least one xylene isomer. Generally, isomerization of a non-equilibrium $C_8$ aromatic feed mixture including xylenes and ethylbenzene to yield para-xylene is a particularly preferred application. Typically, such a mixture may have an ethylbenzene content in the approximate range of about 1% to about 50%, by weight, an ortho-xylene content in the approximate range of about 0 to about 90%, by weight, a meta-xylene content in the approximate range of about 0 to about 95%, by weight, and a para-xylene content in the approximate range of about 0 to about 30%, by weight. In some embodiments, the aromatic feed mixture may also include some level of $A_9$-$A_{11+}$ aromatics as well as some amounts of benzene and toluene as well.

The alkylaromatic containing streams such as catalytic reformate with or without subsequent aromatic extraction can be isomerized to produce specified xylene isomers and particularly to produce para-xylene. A $C_8$ aromatic feed may contain non-aromatic hydrocarbons, i.e., naphthenes and paraffins, in an amount up to about 30%, by weight. Preferably the isomerizable hydrocarbons consist essentially of aromatics, however, to ensure pure products from downstream recovery processes. Typically, the non-equilibrium alkylaromatic feed mixture is an effluent from a xylene isomer separation zone.

Accordingly, an alkylaromatic hydrocarbon feed mixture may be contacted with a catalyst respectively in a $C_8$ isomerization zone. Typically, the isomerization stage is at least for isomerizing at least one xylene and converting ethylbenzene. Contacting may be effected using a fixed-bed system, a moving-bed system, a fluidized-bed system, a slurry system or an ebullated-bed system, or a batch-type operation. Preferably, a fixed-bed system is utilized. The isomerization state includes at least one reactor.

In a preferred manner, the feed mixture is preheated by suitable heating means as known in the art to the desired reaction temperature and passes in a liquid phase in the substantial absence of hydrogen having no externally added hydrogen into the isomerization stage containing at least one fixed reactor having an isomerization catalyst. The isomerization stage may include a single reactor, or two or more separate reactors with suitable measures to ensure that the desired isomerization temperature is maintained at the entrance of each reactor. The reactants may be contacted with the catalyst bed in upward-, downward-, or radial-flow fashion to obtain an intermediate stream that may contain alkylaromatic isomers in a ratio differing from the feed mixture. In the preferred processing of one or more $C_8$ aromatics, the intermediate stream can contain xylenes in proportions closer to equilibrium than in the feed mixture plus ethylbenzene in a proportion relating to the feed mixture.

Generally, the isomerization catalyst includes a molecular sieve, such as a zeolite. The catalyst for the instant claimed subject matter contains no metals. Typically, the zeolite is an aluminosilicate zeolite, having a Si:$Al_2$ ratio greater than about 10, preferably greater than about 18, and a pore diameter of about 5 to about 8 angstroms (Å). Specific examples of suitable zeolites are MEI, MEL, MFFMEL intergrowth, UZM-54, EUO, FER, MFS, MTT, MTW, TON, MOR, and FAU zeolites, as disclosed in US 2007/0004947. One exemplary pentasil zeolite is UZM-54. Another exemplary pentasil zeolite is a layered MEI, which contains a unique a two dimensional layered MFI structure.

The porous microcrystalline material of the isomerization catalyst preferably is composited with a binder. The proportion of binder in the catalyst is about 5% to about 90%, preferably about 10% to about 80%, and optimally about 70%, by weight. Typically, the catalyst can contain about 20% to about 90%, preferably about 70%, by weight, of the aluminosilicate zeolite. In one embodiment the catalyst contains about 70% zeolite and about 30% binder, by weight. In another example, the catalyst may contain about 80% zeolite and about 20% binder, by weight.

Usually catalyst particles are homogeneous with no concentration gradients of the catalyst components. Alternatively, the catalyst particles may be layered, for example, with an outer layer of a bound zeolite bonded to a relatively inert core. Examples of layered catalysts can be found in U.S. Pat. No. 6,376,730 B1 and U.S. Pat. No. 4,283,583.

The binder should be a porous, adsorptive material having a surface area of about 25 $m^2$/g to about 500 $m^2$/g that is relatively refractory to conditions utilized in a hydrocarbon conversion process. Typically, the binder can include (1) a refractory inorganic oxide such as an alumina, a titania, a zirconia, a chromia, a zinc oxide, a magnesia, a thoria, a boria, a silica-alumina, a silica-magnesia, a chromia-alumina, an alumina-boria, or a silica-zirconia; (2) a ceramic, a porcelain, or a bauxite; (3) a silica or silica gel, a silicon carbide, a synthetically prepared or naturally occurring clay or silicate, optionally acid treated, as an example, an attapulgite clay, a diatomaceous earth, a fuller's earth, a kaolin, or a kieselguhr; (4) a crystalline zeolitic aluminosilicate, either naturally occurring or synthetically prepared, such as FAU, MFI, MEL, MFI/MEL intergrowth, UZM-54 MOR, MTW (IUPAC Commission on Zeolite Nomenclature), in hydrogen form or in a form that has been exchanged with metal cations, (5) a spinel, such as $MgAl_2O_4$, $FeAl_2O_4$, $ZnAl_2O_4$, $CaAl_2O_4$, or a compound having a formula $MO—Al_2O_3$ where M is a metal having a valence of 2; or (6) a combination of two or more of these groups.

A preferred refractory inorganic oxide for use as a binder is an alumina or a silica. A suitable alumina material is a crystalline alumina known as a gamma-, an eta-, and a theta-alumina, with a gamma- or an eta-alumina being preferred.

One shape for the support or catalyst can be an extrudate. Generally, the extrusion initially involves mixing of the zeolite with optionally the binder and a suitable peptizing agent to form a homogeneous dough or thick paste having the correct moisture content to allow for the formation of extrudates with acceptable integrity to withstand direct calcination. Extrudability may be determined from an analysis of the moisture content of the dough, with a moisture content in the range of about 30% to about 70%, by weight, being preferred. The dough may then be extruded through a die pierced with multiple holes and the spaghetti-shaped extrudate can be cut to form particles in accordance with known techniques. A multitude of different extrudate shapes is possible, including a cylinder, a cloverleaf, a dumbbell, a trilobe, or a symmetrical or an asymmetrical polylobate. Furthermore, the dough or extrudate may be shaped to any desired form, such as a sphere, by, e.g., marumerization that can entail one or more moving plates or compressing the dough or extrudate into molds.

Alternatively, support or catalyst pellets can be formed into spherical particles by accretion methods. Such a method can entail adding liquid to a powder mixture of a zeolite and binder in a rotating pan or conical vessel having a rotating auger.

Generally, preparation of alumina-bound spheres involves dropping a mixture of molecular sieve, alsol, and gelling agent into an oil bath maintained at elevated temperatures. Examples of gelling agents that may be used in this process include hexamethylene tetraamine, urea, and mixtures thereof. The gelling agents can release ammonia at the elevated temperatures that sets or converts the hydrosol spheres into hydrogel spheres. The spheres may be then withdrawn from the oil bath and typically subjected to specific aging treatments in oil and an ammonia solution to further improve their physical characteristics. One exemplary oil dropping method is disclosed in U.S. Pat. No. 2,620,314.

Preferably, the resulting supports are then washed and dried at a relatively low temperature of about 50° C. to about 200° C. and subjected to a calcination procedure at a temperature of about 450° C. to about 700° C. for a period of about 1 hour to about 20 hours.

Optionally, the catalyst is subjected to steaming to tailor its acid activity. The steaming may be effected at any stage of the zeolite treatment. Steaming conditions can include a water concentration of about 5% to about 100%, by volume, pressure of about 100 kPa to about 2 MPa, and a temperature of about 600° C. to about 1200° C. Preferably, the steaming temperature is about 650° C. to about 1000° C., more preferably at least about 750° C., and optimally may be at least about 775° C. In some cases, temperatures of about 800° C. to at least about 850° C. may be employed. The steaming should be carried out for a period of at least one hour, and periods of about 6 hours to about 48 hours are preferred. Alternatively or in addition to the steaming, the composite may be washed with one or more solutions of an ammonium nitrate, a mineral acid, or water. The washing may be effected at any stage of the preparation, and two or more stages of washing may be employed. The catalyst can contain at least about 30%, preferably about 30% to about 50%, by weight, silicon, calculated on an elemental basis based on the catalyst.

The alkylaromatic feed mixture contacts the isomerization catalyst in the liquid phase at suitable first isomerization conditions. Such conditions can include a temperature ranging from about 180° C. to about 600° C., preferably from about 215° C. to about 350° C. Generally, the pressure is sufficient to maintain the feed mixture in liquid phase, generally from about 500 kPa to about 5 MPa. The isomerization stage can contain a sufficient volume of catalyst to provide a weight hourly space velocity with respect to the feed mixture of about 0.5 $hr^{-1}$ to about 50 $hr^{-1}$, preferably about 0.5 $hr^{-1}$ to about 20 $hr^{-1}$.

An exemplary zeolitic molecular-sieve component of the isomerization catalyst can be a high meso-surface area, low silicon/alumina ratio pentasil zeolite, also characterized as UZM-54. Alternatively, the exemplary catalyst can be a two dimensional layered MFI framework type according to the ATLAS OF ZEOLITE STRUCTURE TYPES, such as the molecular sieve as disclosed in U.S. patent application Ser. No. 14/636,624. In another embodiment, a layered MFI may be used, which is a two dimensional layered MFI structure, as disclosed in U.S. patent application Ser. No. 14/636,541.

The isomerized product from the isomerization stage can include a concentration of at least one alkylaromatic isomer that is higher than the equilibrium concentration at the isomerization conditions. Desirably, the isomerized product in a line is a mixture of one or more $C_8$ aromatics having a concentration of para-xylene that is higher than the equilibrium concentration at isomerization conditions. The concentration of para-xylene can be at least about 23%, often at least about 24%, and may be at least about 25%, by weight. The $C_8$ aromatic ring loss relative to the feed mixture (defined hereinafter) is usually less than about 0.5%, preferably less than about 0.2%, by weight.

The isomerized product can be fed to a separation zone. The separation zone can be one or more distillation towers, solvent extractors, and/or mol sieve separators. An exemplary separation zone utilizing fractionation is disclosed in U.S. Pat. No. 3,835,198. The isomerized product is sent to the separation zone to obtain a lighter stream containing naphthenes and a heavier stream in a line. Typically the heavier stream can contain xylenes and ethylbenzene. In many aromatic production facilities, this stream can be recycled back to the xylene isomer separation zone after further processing, such as fractionation. The lighter stream can contain $C_8$ naphthenes, benzene, and toluene. The benzene and toluene can be withdrawn as a vapor phase stream from an overhead receiver from a column in the separation zone, as disclosed in U.S. Pat. No. 4,783,568.

The elemental analysis of the catalyst components can be determined by Inductively Coupled Plasma (ICP) analysis. Some components, such as zeolite or binder where each may contain silica, or silicon can be measured by UOP Method 961-98.

All the UOP methods, such as UOP-873-86 and UOP-961-98 discussed herein, can be obtained through ASTM International, 100 Barr Harbor Drive, West Conshohocken, Pa., USA.

Illustrative Embodiments

The following examples are intended to further illustrate the subject process. These illustrations of embodiments of the claimed subject matter are not meant to limit the claims of this claimed subject matter to the particular details of these examples. These examples are based on engineering calculations and actual operating experience with similar processes.

The FIGURE illustrates a stability comparison for the liquid phase isomerization catalyst. Run A includes a catalyst having UZM-54 with a silica binder in the presence of hydrogen. Run A includes a catalyst having UZM-54 with a silica binder with no hydrogen. Run C includes a catalyst having UZM-54 with an alumina binder in the presence of hydrogen. Run D includes a catalyst having UZM-54 with an alumina binder with no hydrogen.

The FIGURE illustrates that as the catalyst deactivates with time, the paraxylene to xylene ratio goes down and hence the relative activity drops. For a silica bound catalyst, as shown in run A, performance goes down with increasing DOS even in presence of hydrogen. On elimination of hydrogen, performance further gets worse, as shown in run B. For an alumina bound catalyst, shown in run C, stability performance is excellent. Additionally, the performance remains unaffected even if hydrogen is eliminated, as shown in D. The FIGURE illustrates improved stability even in the absence of hydrogen, which allows for the elimination of hydrogen from the LPISOM process. Overall, the FIGURE illustrates that UZM-54 with alumina binder shows improved stability even in the absence of hydrogen and therefore allows elimination of hydrogen in liquid phase xylene isomerization.

Without further elaboration, it is believed that one skilled in the art can, using the preceding description, utilize the present claimed subject matter to its fullest extent. The preceding preferred specific embodiments are, therefore, to be construed as merely illustrative, and not limitative of the remainder of the disclosure in any way whatsoever.

In the foregoing, all temperatures are set forth uncorrected in degrees Celsius and, all parts and percentages are by weight, unless otherwise indicated. From the foregoing description, one skilled in the art can easily ascertain the essential characteristics of this claimed subject matter and, without departing from the spirit and scope thereof, can make various changes and modifications of the claimed subject matter to adapt it to various usages and conditions.

Specific Embodiments

While the following is described in conjunction with specific embodiments, it will be understood that this description is intended to illustrate and not limit the scope of the preceding description and the appended claims.

A first embodiment of the invention is a process for the isomerization of an alkylaromatic feed mixture, comprising contacting the alkylaromatic feed mixture in a $C_8$ isomerization zone, wherein the $C_8$ isomerization zone comprises an isomerization stage wherein the alkylaromatic feed mixture contacts a catalyst comprising a UZM-54, a binder, and an absence of metals, at isomerization conditions in a liquid phase in the substantial absence of hydrogen to produce a product stream. An embodiment of the invention is one, any or all of prior embodiments in this paragraph up through the first embodiment in this paragraph, wherein the binder may be alumina. An embodiment of the invention is one, any or all of prior embodiments in this paragraph up through the first embodiment in this paragraph, wherein the catalyst contains about 50% to about 90% UZM-54 by weight. An embodiment of the invention is one, any or all of prior embodiments in this paragraph up through the first embodiment in this paragraph, wherein the catalyst contains about 70% UZM-54 by weight. An embodiment of the invention is one, any or all of prior embodiments in this paragraph up through the first embodiment in this paragraph, wherein the isomerization conditions include a temperature of about 200° C. to about 320° C. An embodiment of the invention is one, any or all of prior embodiments in this paragraph up through the first embodiment in this paragraph, wherein the isomerization conditions include a pressure sufficient to maintain LPI feed in liquid phase. An embodiment of the invention is one, any or all of prior embodiments in this paragraph up through the first embodiment in this paragraph, wherein the isomerization conditions include a weight hourly space velocity of about 1 $hr^{-1}$ to about 15 $hr^{-1}$. An embodiment of the invention is one, any or all of prior embodiments in this paragraph up through the first embodiment in this paragraph, wherein the product stream comprises a paraxylene to xylene ratio of about 20 wt % to about 24 wt %. An embodiment of the invention is one, any or all of prior embodiments in this paragraph up through the first embodiment in this paragraph, wherein the product stream comprises a paraxylene to xylene ratio of about 23 wt %. An embodiment of the invention is one, any or all of prior embodiments in this paragraph up through the first embodiment in this paragraph, wherein the process takes place in a fixed bed reactor.

A second embodiment of the invention is a process for the isomerization of an alkylaromatic feed mixture, comprising contacting the alkylaromatic feed mixture in a $C_8$ isomerization zone, wherein the $C_8$ isomerization zone comprises an isomerization stage wherein the alkylaromatic feed mixture contacts a catalyst comprising a layered MFI, a binder, and an absence of metals, at isomerization conditions in a liquid phase in the substantial absence of hydrogen to produce a product stream. An embodiment of the invention is one, any or all of prior embodiments in this paragraph up through the second embodiment in this paragraph, wherein the binder may be alumina. An embodiment of the invention is one, any or all of prior embodiments in this paragraph up through the second embodiment in this paragraph, wherein the catalyst contains about 50% to about 90% layered MFI by weight. An embodiment of the invention is one, any or all of prior embodiments in this paragraph up through the second embodiment in this paragraph, wherein the catalyst contains about 70% layered MFI by weight. An embodiment of the invention is one, any or all of prior embodiments in this paragraph up through the second embodiment in this paragraph, wherein the isomerization conditions include a temperature of about 200° C. to about 320° C. An embodiment of the invention is one, any or all of prior embodiments in this paragraph up through the second embodiment in this paragraph, wherein the isomerization conditions include a pressure sufficient to maintain LPI feed in liquid phase. An embodiment of the invention is one, any or all of prior embodiments in this paragraph up through the second embodiment in this paragraph, wherein the isomerization conditions include a weight hourly space velocity of about 1 $hr^{-1}$ to about 15 $hr^{-1}$. An embodiment of the invention is one, any or all of prior embodiments in this paragraph up through the second embodiment in this paragraph, wherein the product stream comprises a paraxylene to xylene ratio of about 20 wt % to about 24 wt %. An embodiment of the invention is one, any or all of prior embodiments in this paragraph up through the second embodiment in this paragraph, wherein the product stream comprises a paraxylene to xylene ratio of about 23 wt %. An embodiment of the invention is one, any or all of prior embodiments in this paragraph up through the second embodiment in this paragraph, wherein the process takes place in a fixed bed reactor.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for the isomerization of an alkylaromatic feed mixture, comprising contacting the alkylaromatic feed mixture in a $C_8$ isomerization zone, wherein the $C_8$ isomerization zone comprises an isomerization stage wherein the alkylaromatic feed mixture contacts a catalyst comprising a UZM-54 zeolite, alumina, and an absence of metals, at isomerization conditions in a liquid phase in the complete absence of hydrogen to produce a product stream.

2. The process of claim 1, wherein the catalyst contains about 50% to about 50% to about 90% UZM-54 zeolite by weight.

3. The process of claim 1, wherein the catalyst contains about 70% UZM-54 zeolite by weight.

4. The process of claim 1, wherein the isomerization conditions include a temperature of about 200° C. to about 320° C.

5. The process of claim 1, wherein the isomerization conditions include a pressure sufficient to maintain the alkylaromatics feed mixture in liquid phase.

6. The process of claim 1, wherein the isomerization conditions include a weight hourly space velocity of about 1 $hr^{-1}$ to about 15 $hr^{-1}$.

7. The process of claim 1, wherein the product stream comprises a paraxylene to xylene ratio of about 20 wt % to about 24 wt %.

8. The process of claim 1, wherein the product stream comprises a paraxylene to xylene ratio of about 23 wt %.

* * * * *